United States Patent [19]

Throckmorton et al.

[11] 4,243,612
[45] Jan. 6, 1981

[54] BENZYLIC OXIDATION PROCESS

[75] Inventors: Peter E. Throckmorton, Plain City; Gary E. Sitz, Marysville; Robert A. Grimm, Upper Arlington, all of Ohio

[73] Assignee: Ashland Oil, Inc., Ashland, Ky.

[21] Appl. No.: 66,196

[22] Filed: Aug. 13, 1979

[51] Int. Cl.³ ............................................... C07C 45/36
[52] U.S. Cl. .................................. 568/431; 252/469; 252/470; 252/467; 252/468
[58] Field of Search .......................... 260/599, 604 R; 252/467, 468, 469, 470

[56] References Cited
U.S. PATENT DOCUMENTS

| | | | |
|---|---|---|---|
| 3,579,589 | 5/1971 | Delman | 260/599 |
| 3,714,263 | 1/1973 | Cyba | 260/599 |
| 3,859,358 | 1/1975 | Grasselli et al. | 260/604 R |
| 3,933,751 | 1/1976 | Callahan et al. | 260/604 R |

OTHER PUBLICATIONS

Ai et al., Chem. Abst., vol. 77, #66559k (1977).

*Primary Examiner*—James H. Reamer

[57] ABSTRACT

A vapor phase process for the direct oxidation of a methyl benzene to the corresponding aldehyde derivative; e.g., conversion of toluene to benzaldehyde, wherein said oxidation is effected in the presence of a catalyst system consisting essentially of uranium and molybdenum oxides in combination with an oxide of lead, tin, zirconium, cadmium, antimony or nickel.

5 Claims, No Drawings

BENZYLIC OXIDATION PROCESS

BACKGROUND OF THE INVENTION

1. Field of the Invention

This invention relates to a process for the production of aromatic aldehydes.

2. Description of the Prior Art

Aromatic aldehydes, particularly representative of which is benzaldehyde, find widespread usefulness as intermediates in the manufacture of perfumes, dyes, drugs and like specialty products. The prior art method for the production of benzaldehyde for the foregoing uses involves the chlorination of toluene followed by the hydrolysis of the resultant dichlorinated derivative. This method is beset with difficulties which translates to the fact that it is a relatively costly way of producing this intermediate.

Recently, investigative interest has centered on potential ways for producing styrene from toluene because of the increasing availability of toluene as opposed to that of benzene and the ever mounting cost of ethylene. An applicable route of this nature involves the conversion of toluene to benzyl alcohol followed by a homologation step to provide phenethanol which upon dehydration yields styrene. The most refractory reaction in the sequence is the conversion of toluene to benzyl alcohol. This conversion can be fairly readily achieved by acetyloxylating toluene followed by hydrolysis but at the considerable sacrifice of introducing highly corrosive acetic acid into the reaction system.

The direct oxidation of toluene to benzyl alcohol has to date proven to be an elusive desideratum insofar as the oxidation reaction is essentially completely selective toward the formation of the aldehyde. Accordingly, one is constrained to hydrogenate the aldehyde in order to obtain styrene ultimately which procedure nonetheless augurs to be an overall improvement over the acetyloxylation route.

As indicated previously, the method of producing benzaldehyde via the chlorination of toluene is costly and thus economically unacceptable for any scheme in deriving therefrom a commodity chemical such as stryene. The direct oxidation method, while potentially attractive, has long suffered in practice because all of the catalysts purported to be useful for this purpose provided unacceptively low selectivity and conversion. However, a noteworthy advance in this area of technology was to be found in U.S. Pat. No. 3,579,589. Therein it is essentially taught that a combination or uranium and molybdenum oxides represent an effective catalyst system for conversion of toluene to benzaldehyde. The object of this invention is that of modifying the aforesaid catalyst system with a promoter metal so as primarily to enhance substantially the selectivity characteristics thereof.

SUMMARY OF THE INVENTION

In accordance with the present invention a catalyst system is provided which exhibits improved selectivity toward the formation of benzaldehyde in the vapor phase oxidation of toluene. The gram-atom empirical formula for the contemplated catalysts in the broadest aspect of the invention is as follows:

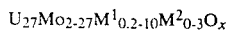

$$U_{27}Mo_{2-27}M^1_{0.2-10}M^2_{0-3}O_x$$

wherein $M^1$ is lead, tin, zirconium, cadmium, antimony, nickel or mixtures thereof; $M^2$ represents potassium or sodium and x represents the amount of oxygen bound to the other elements in their respective states of oxidation in the catalyst system.

DESCRIPTION OF THE PREFERRED EMBODIMENTS

The catalysts useful in the practice of this invention are obtained by combining appropriate compounds of the applicable constituent metals with a strong mineral acid. After digestion or solublization of the metal compounds, as the case may be depending upon the nature of the acid utilized, the resultant metal composite is calcined in the presence of an oxidizing atmosphere. The preferred mineral acids are sulfuric and hydrochloric. In the use of sulfuric acid, the applicable metal compounds are combined to form a limpid paste which is then subsequently calcined.

A variety of uranyl salts; e.g., sulfate, nitrate, etc., as well as the oxides of uranium represent suitable sources for this metal. Particularly suitable uranyl compounds are the nitrate salts and oxides or a combination thereof. With regard to molybdenum compounds, the molybdates or paramolybdates of ammomium are applicable. The contemplated alkali or alkaline earth metal component of the catalyst compositions useful herein is preferably that of the nitrate salt. Various amounts of the metal constituents in the form of their salts or oxides as aforesaid are combined in relative proportions so as to provide a gram-atomic relationship between the indicated metals in keeping with the empirical formula hereinabove set forth. Upon calcination, this relationship will only be minorly affected.

The use of hydrochloric acid likewise involves the use of the preferred metal compounds noted above. In this instance a solution of the combined metal compounds is effected, then evaporated to dryness and calcined in the manner discussed in connection with the use of sulfuric acid. A calcination temperature applicable for deriving the catalyst system ranges between about 500°–700° C. and preferably in the order of about 600° C. During calcination, a moderate flow of air is desirably maintained over the heated mass. Complete calcination is normally realized in about 4–6 hours of heating. Following calcination, the resultant catalyst is ground to provide a particulate form thereof which can be employed as such, or if desired, converted to pellets. A preferred practice is to admix the catalyst with a suitable diluent such as alumina or silica gel of approximately the same particle size as that of the calcined catalyst. Silica gel is the preferred diluent and is utilized in an amount to provide 25–75% of the total composition on a volumetric basis.

While the discussion presented hereinabove has primarily centered on the use of the catalyst systems of this invention for effecting the vapor phase oxidation of toluene, the substrate is not limited to this particular methyl benzene. Other methyl benzenes are any of those which have a ring substituent which does not interfere with the underlying oxidation reaction. Representative of applicable substrates other than toluene are such as p-chloro toluene, p-methoxy-toluene and the like. The oxidation reaction is carried out at an elevated temperature in the range from about 550°–650° C. While air can be employed to effect oxidation, a preformed mixture of nitrogen and oxygen containing from 5 to 20 vol. % oxygen represents the preferred procedure for introducing the latter. The preferred mixture of the oxidant gas contains in the order of about 10% oxygen. The oxygen is combined with the methyl benzene, specifically toluene, desirably on the stoichiometrical basis; i.e., one mole of gaseous oxygen per mole of toluene. However, up to 30% deficiency of the stoichiometric requirement of oxygen can be used if desired.

The use of water in the form of steam as the co-feed for toluene represents a desirable expedient to aid in the dissipation of heat thereby minimizing combustion of the toluene. Water, when used in this manner, can be introduced in the amount of 50 to 200% of the moles of toluene introduced into the reaction. Contact or residence time of the reaction is desirably in the order of about 0.5 seconds as measured on an empty reactor basis at reaction temperature. An operating range of contact time is from about 0.25–1.5 seconds. The foregoing serves as a general rundown on the more important reaction parameters encountered in the use of the catalyst systems herein for effecting the oxidation of toluene to benzaldehyde. A more complete insight as to the operational conditions involved can be found in a plurality of the working exemplications to follow.

EXAMPLE I

The purpose of this and the succeeding example is to illustrate two varied techniques for preparing a catalyst useful in the practice of this invention.

To a mixture of 38.0 g (0.0757 mol) of uranyl nitrate hexahydrate [$UO_2(NO_3)_2 \cdot 6H_2O$] and 47.8 g (0.0536 mol) of uranium oxide ($U_3O_8$) was added 8.00 g (0.00647 mol) of ammonium heptamolybdate hexahydrate [$(NH_4)_6Mo_7O_{24} \cdot 6H_2O$] and 0.90 g (0.00891 mol) of potassium nitrate ($KNO_3$) and 2.40 g (0.00725 mol) of lead nitrate.

The mixture was ground with 24 ml of concentrated sulfuric acid to form a paste. The paste was charged to a fused quartz tube to form an elongated layer therein. With 300 ml/min. air flowing over the surface of the paste, the quartz tube was heated for 6 hours at 600° C. The calcined solid was cooled and lightly ground to provide particulates having a Standare Sieve size of 40–60 mesh.

Analysis indicated the folowing weight composition: 3.61% Mo, 2.44% Pb, 0.23% K, 28.45% O, 6.87% S and 58.5% U. The gram-atomic proportions of this analysis relative to 27 gram-atomic proportions of uranium are expressed in the following relationship in which the indicated sulfur content is omitted:

$$U_{27}Mo_{4.13}Pb_{1.30}K_{0.65}O_x$$

The corresponding gram-atomic proportions calculated for the starting materials prior to calcination is as follows:

$$U_{27}Mo_{5.17}Pb_{0.83}K_{1.02}O_x$$

The BET surface area of the catalyst measured 0.5 m²/g. Residual sulfur present in the calcined product was determined by X-ray to exist as the beta form of uranyl sulfate. Subsequent X-ray study showed that the indicated sulfur was lost once the catalyst was conditioned for a brief period in an oxidation reaction at 600° C. in the course of which the uranium was converted to $U_3O_8$. Thermogravimetric analysis (TGA) of the fresh calcined catalyst showed continuous weight loss until 700° C. and essentially no weight loss commencing at 800° C. The weight loss was consistent with the decomposition of $UO_2SO_4$ of the fresh calcined catalyst to form uranyl oxide with loss of sulfur as oxide.

EXAMPLE II

Uranium nitrate hexahydrate in the amount of 90.0 g (0.1793 mol), together with 5.88 g (0.00473 mol) of ammonium heptamolybdate hexahydrate and 1.50 g (0.00665 mol) of stannous chloride dihydrate ($SnCl_2 \cdot 2H_2O$) were dissolved in 450 ml of 0.5 N hydrochloric acid along with 0.67 g (0.00663 mol) of potassium nitrate. The resultant solution was evaporated under vacuum in a rotating flask to partly dry uniform granular solids. The wet mixture was charged to a fused quartz tube in the manner described in Example I and calcined at 600° C. for 4 hours employing a 300 ml air flow rate. The calcined catalyst was cooled and ground lightly to a 20–35 mesh size. The gram-atomic proportions calculated from the materials charged relative to 27 gram-atoms of uranium are expressed in the following relationship:

$$U_{27}Mo_{5.0}Sn_{1.0}K_{1.0}O_x$$

EXAMPLE III

A catalyst system in accordance with this invention wherein zirconium served as a promoter metal was prepared following the procedure of Example I. The gram-atomic relationship between the constituent metals prior to calcination was as follows:

$$U_{27}Mo_5Zr_1K_1O_x$$

EXAMPLE IV

Following the procedure of Example I, a catalyst was prepared in which the lead nitrate was omitted from the overall composition and as such served to provide the control oxidation run (Run No. 7) outlined in the following Example V. The relative gram-atomic proportions of the constituent metals prior to calcination bore the relationship as follows:

$$U_{27}Mo_5K_{1.5}O_x$$

EXAMPLE V

This example illustrates the use of the catalyst preparations of the foregoing examples in effecting the vapor phase oxidation of toluene to benzaldehyde. The reactor as well as the general manner of conducting the reaction was the same for each of the enumerated runs. The procedure observed consisted of feeding a preheated mixture of toluene, oxygen and nitrogen gases, as well as steam where employed, at 240°–280° C. through a stainless steel tube of ⅜ inch OD (9/32 inch ID) and approximately 20-inch in length containing the test catalyst as a packed bed maintained at 600° C. The packed bed in each instance consisted of a 20 ml volume of the catalyst/silica mixture. As indicated previously, mixtures of the catalyst with above similar sized silica gel diluent represents the preferred manner of utilizing the catalyst.

The pre-heater consisted of a length of stainless steel tube similar to the reactor but packed with glass beads. The pressure noted for the various runs was observed at the inlet of the reactor. Effluent from the reactor tube was condensed in dry ice traps and any carbon dioxide formed during the course of oxidizing the toluene was absorbed in an Ascarite tube protected by a calcium sulfate absorber for any uncondensed water. The condensed organic product was separated from the water collected and analyzed by the internal standard method of gas chromatography.

Other pertinent processing conditions observed for the individual runs as well as the identity of the catalyst used therein are set forth in Table IA presented hereinbelow. Table IB complements Table I A in providing the analysis results obtained in carrying out each of the oxidation runs.

in which $M^1$ is lead, tin, zirconium, cadmium, antimony or nickel; $M^2$ is sodium or potassium and x represents the amount of oxygen bound to the other elements in their respective states of oxidation in the catalyst system.

2. The improvement in accordance with claim 1 wherein $M^1$ is lead and $M^2$ is potassium.

3. The improvement in accordance with claim 1 wherein said catalyst system has the empirical formula:

TABLE IA

| | | | | | | CHARGE TO REACTOR | | | | |
| | | | | | | TOLUENE | | GASES | | |
| RUN No. | CATALYST | PRESS. (psig) | TEMP. (°C.) | SILICA (% vol) | Rx TIME[a] (sec) | amt. (g) | rate (ml/min) | $O_2$ (ml/min) | $N_2$ (ml/min) | WATER (ml/min) |
| --- | --- | --- | --- | --- | --- | --- | --- | --- | --- | --- |
| 1 | Example I | 10.5 | 605 | 25 | 0.56 | 35 | 0.41 | 50 | 650 | 0 |
| 2 | " | 10.5 | 595 | 25 | 0.52 | 35 | 0.46 | 65 | 650 | 0 |
| 3 | " | 4.0 | 590 | 25 | 0.74 | 71 | 0.32 | 40 | 380 | 0.07 |
| 4 | " | 4.0 | 613 | 25 | 0.59 | 34 | 0.31 | 44 | 430 | 0.09 |
| 5 | Example II | 2.5 | 600 | 25 | 0.86 | 39 | 0.34 | 36 | 430 | 0.08 |
| 6 | Example III | 13.0 | 593 | 25 | 0.83 | 29 | 0.15 | 39 | 440 | 0 |
| 7 | Example IV | 2.0 | 600 | 50 | 0.71 | 115 | 0.32 | 40 | 380 | 0 |

[a]Rx time = contact time on empty tube basis @Rx temperature

TABLE IB

| | EFFLUENT ANALYSIS LESS ADDED WATER | | | | | | | | BALD[c] | TOLUENE |
| RUN | LIQUID ORGANIC CONDENSATE (L) | | | | | $H_2O$ | $CO_2$ | TOLUENE[b] | SELECT. | ACC. |
| No. | AMT. (g) | TOL. (%) | BALD (%) | BENZ. (%) | UNK (%) | (g) | (G) | CONV. (%) | % | FOR (%) |
| --- | --- | --- | --- | --- | --- | --- | --- | --- | --- | --- |
| 1 | 32.2 | 82.1 | 16.9 | 0 | 0 | 0.5 | 0.3 | 15 | 92 | 90 |
| 2 | 28.9 | 80.6 | 19.4 | 0 | 0 | 1.4 | 0.7 | 16 | 87 | 83 |
| 3 | 70.3 | 87.0 | 12.1 | 0 | 0.9 | 2.6 | 0 | 13 | 79 | 99 |
| 4 | 29.3 | 86.5 | 12.9 | 0.7 | 0 | 0.2 | 4.2 | 16 | 62 | 88 |
| 5 | 36.6 | 86.0 | 12.6 | 0.5 | 0.9 | 2.3 | 4.5 | 18 | 55 | 98 |
| 6 | 21.6 | 52.4 | 42.2 | 0 | 5.4 | 5.6 | 0.5 | 58 | 60 | 86 |
| 7 | 102 | 95.5 | 1.8 | 0 | 2.8 | 3.2 | 4.1 | 7 | 19 | 92 |

[b]CONVERSION = $\dfrac{\text{TOL. CONSUMED}}{\text{TOL. CHARGED}}$

Toluene consumed is taken as equivalent of products found plus equivalent of ½ net $H_2O$ from unknown byproducts

[c]BENZALDEHYDE (BALD) SELECT. = $\dfrac{\text{MOL BALD FOUND}}{\text{MOL TOLUENE CONSUMED}}$

What is claimed is:

1. In a catalytic vapor phase process for the oxidation of toluene by reaction with molecular oxygen in the presence of a heterogeneous catalyst system of uranium and molybdenum oxides to effect conversion thereof to benzaldehyde; the improvement wherein said catalyst system has the gram-atom empirical formula:

$$U_{27}Mo_{2-27}M^1_{0.2-10}M^2_{0-3}O_x$$

$$U_{27}Mo_{3-6}M^1_{1-2}M^2_{0.5-1.5}O_x.$$

4. The improvement in accordance with claim 3 wherein $M^1$ is lead and $M^2$ is potassium.

5. The improvement in accordance with claim 4 wherein said catalyst system has the empirical formula:

$$U_{27}Mo_{4.5}Pb_{1-1.5}K_{0.5-1.5}O_x.$$

* * * * *